US009393122B2

United States Patent
Whitaker et al.

(10) Patent No.: US 9,393,122 B2
(45) Date of Patent: *Jul. 19, 2016

(54) MOBILE BEARING HIP ASSEMBLY AND METHOD OF PERFORMING AN ORTHOPAEDIC SURGICAL PROCEDURE

(71) Applicant: DePuy Synthes Products, Inc., Raynham, MA (US)

(72) Inventors: Dustin R. Whitaker, Akron, IN (US); Todd D. Render, Fort Wayne, IN (US); Matthew R. Dressler, Fort Wayne, IN (US)

(73) Assignee: DEPUY SYNTHES PRODUCTS, INC., Raynam, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/722,946

(22) Filed: May 27, 2015

(65) Prior Publication Data

US 2015/0250596 A1 Sep. 10, 2015

Related U.S. Application Data

(63) Continuation of application No. 14/314,809, filed on Jun. 25, 2014, now Pat. No. 9,066,803, which is a continuation of application No. 13/435,514, filed on Mar. 30, 2012, now Pat. No. 8,771,366.

(51) Int. Cl.
*A61F 2/32* (2006.01)
*A61F 2/34* (2006.01)
*A61F 2/36* (2006.01)
*A61F 2/30* (2006.01)

(52) U.S. Cl.
CPC ... *A61F 2/34* (2013.01); *A61F 2/32* (2013.01); *A61F 2/3601* (2013.01); *A61F 2/3609* (2013.01); *A61F 2002/30354* (2013.01); *A61F 2002/30364* (2013.01);

(Continued)

(58) Field of Classification Search
CPC ..... A61F 2/32; A61F 2/34; A61F 2002/3216; A61F 2002/3283; A61F 2002/3291; A61F 2002/3411; A61F 2002/3448; A61F 2002/345; A61F 2002/3208
See application file for complete search history.

(56) References Cited

U.S. PATENT DOCUMENTS

| 5,888,207 A | 3/1999 | Nieder et al. |
| 7,108,720 B2 | 9/2006 | Hanes |

(Continued)

FOREIGN PATENT DOCUMENTS

| EP | 0867158 | 9/1998 |
| FR | 2357235 | 2/1978 |

OTHER PUBLICATIONS

Patent Cooperation Treaty International Search Report, International Application No. PCT/US2013/033117 dated Jul. 1, 2013, 5 pages.

*Primary Examiner* — David Isabella
*Assistant Examiner* — Dinah Baria
(74) *Attorney, Agent, or Firm* — Barnes & Thornburg LLP

(57) ABSTRACT

An acetabular hip implant includes an acetabular shell component, a first insert secured to the acetabular shell component, a second insert secured to the first insert, and a femoral head configured to be secured to the second insert. The first insert is permitted to rotate relative to the acetabular shell about a first axis, the second insert is permitted to rotate relative to the first insert about a second axis, and the femoral head is permitted to rotate relative to the second insert about a third axis. A method for performing an orthopedic surgical procedure on an acetabulum of a patient is also disclosed.

9 Claims, 10 Drawing Sheets

(52) U.S. Cl.
CPC ............ *A61F 2002/30635* (2013.01); *A61F 2002/30662* (2013.01); *A61F 2002/3208* (2013.01); *A61F 2002/3216* (2013.01); *A61F 2002/3403* (2013.01); *A61F 2002/345* (2013.01); *A61F 2002/3412* (2013.01); *A61F 2002/3448* (2013.01); *A61F 2002/3617* (2013.01); *A61F 2310/00011* (2013.01)

(56) References Cited

U.S. PATENT DOCUMENTS

| | | | |
|---|---|---|---|
| 7,115,145 B2 * | 10/2006 | Richards | A61F 2/32 623/18.11 |
| 2004/0193282 A1 | 9/2004 | Hanes | |
| 2009/0192610 A1 | 7/2009 | Case et al. | |

* cited by examiner

MOBILE BEARING HIP ASSEMBLY AND METHOD OF PERFORMING AN ORTHOPAEDIC SURGICAL PROCEDURE

CROSS REFERENCE TO RELATED APPLICATION

This application is a continuation of U.S. patent application Ser. No. 14/314,809, now U.S. Pat. No. 9,066,803, filed Jun. 25, 2014, which is a continuation of U.S. patent application Ser. No. 13/435,514, now U.S. Pat. No. 8,771,366, filed Mar. 30, 2012, the contents of each of which are incorporated herein by reference.

TECHNICAL FIELD

The present disclosure relates generally to prosthetic orthopaedic implants, and more particular, to orthopaedic hip implants.

BACKGROUND

Many orthopaedic procedures involve the implantation of prosthetic devices to replace badly damaged or diseased joint tissue. Common orthopaedic procedures that involve prosthetic devices include total or partial hip, knee, and shoulder replacements. Hip replacement involves total or partial replacement of the hip ball and socket joint.

A total hip replacement procedure typically involves the implantation of two main component systems: a femoral component and an acetabular component. The femoral component includes a rigid stem that is anchored within the patient's femur and also includes a head that replaces the patient's natural femoral head. The acetabular component is implanted within the acetabulum of the patient and serves as a bearing surface for the head of the femoral component. The acetabular component generally includes an outer shell configured to engage the acetabulum of the patient and an inner bearing or liner coupled to the shell and configured to engage the femoral head. The femoral head and inner liner of the acetabular component form a ball and socket joint that approximates the natural hip joint.

SUMMARY

According to an illustrative embodiment, a method for performing an orthopaedic surgical procedure on an acetabulum of a patient comprises the steps of securing an acetabular shell component to an acetabulum of a patient and securing a first insert to an acetabular shell component configured to be implanted within an acetabulum of a patient. The method may further include the steps of allowing the first insert to rotate relative to the acetabular shell component about a first axis and preventing rotation of the first insert relative to the acetabular shell component about a second axis and a third axis, the first insert having a first set of discrete opposing flats defined in its inner surface on opposing sides of the first insert, wherein flats of the first set of opposing flats are not connected to one another.

Still further, the method may include the step of securing a second insert to the first insert such that the outer surface of the second insert contacts the inner surface of the first insert, the second insert having a second set of discrete opposing flats defined in its outer surface on opposing sides of the second insert, wherein flats of the second set of opposing flats are not connected to one another and wherein the second set of opposing flats contact the first set of opposing flats defined in the inner surface of the first insert. The method may also include the steps of allowing relative rotation between the second insert and the first inset about the second axis and preventing relative rotation between the second insert and the first insert about the first axis and the third axis, the second insert having a third set of discrete opposing flats defined in its inner surface on opposing sides of the second insert, wherein flats of the third set of opposing flats are not connected to one another.

Still further, the method may include the steps of securing a femoral head configured to be secured to a femoral stem to the second insert such that the outer surface of the femoral head contacts the inner surface of the second insert, the femoral head having a fourth set of discrete opposing flats defined in its outer surface on opposing sides of the femoral head, wherein flats of the fourth set of opposing flats are not connected to one another and wherein the fourth set of opposing flats contact the third set of opposing flats defined in the inner surface of the second insert, allowing relative rotation between the femoral head and the second insert about the third axis, and preventing relative rotation between the femoral head and the second insert about the first axis and the second axis.

The step of securing the acetabular shell component to the acetabulum of a patient may occur before the steps of securing the first insert to the acetabular shell component, securing the second inset to the first insert, and securing the femoral head to the second insert.

The steps of securing the first insert to the acetabular shell component and securing the second insert to the first insert may occur before the step of securing the acetabular shell component to the acetabulum of the patient.

The method may further includes the step of reaming the acetabulum of the patient to form a hemispherically shaped cavity prior to securing the acetabular shell component to the acetabulum of the patient.

The step of securing the acetabular shell component to the acetabulum of the patient may include press fitting, bolting, or cementing the acetabular shell component to the acetabulum.

The step of allowing the first insert to rotate relative to the acetabular shell component about a first axis may include the step of inserting a cylindrical wall extending outwardly from the first insert into an aperture formed in the acetabular shell component.

The step of allowing the first insert to rotate relative to the acetabular shell component about a first axis may include the step of aligning a projection extending outwardly from the acetabular shell component with a recess formed in the first insert.

The step of allowing the first insert to rotate relative to the acetabular shell component about a first axis may include the step of aligning a projection extending outwardly from the first insert with a recess formed in the acetabular shell component.

The method may further include the steps of orienting the first axis to be orthogonal to the second axis and the third axis and orienting the second axis to be orthogonal to the third axis.

According to another illustrative embodiment, a method for performing an orthopaedic surgical procedure on an acetabulum of a patient comprises the steps of securing an acetabular shell component to an acetabulum of a patient and securing a first insert to an acetabular shell component configured to be implanted within an acetabulum of a patient, such that the first insert is (i) permitted to rotate relative to the acetabular shell component about a first axis, and (ii) prevented from rotating relative to the acetabular shell component about a second axis and a third axis, the first insert having a first set of discrete opposing flats defined in its inner surface on opposing sides of the first insert, wherein flats of the first set of opposing flats are not connected to one another.

The method further includes the step of securing a second insert to the first insert such that the outer surface of the second insert contacts the inner surface of the first insert, the second insert having a second set of discrete opposing flats defined in its outer surface on opposing sides of the second insert, wherein flats of the second set of opposing flats are not connected to one another and wherein the second set of opposing flats contact the first set of opposing flats defined in the inner surface of the first insert such that the second insert is (i) permitted to rotated relative to the first insert about the second axis, and (ii) prevented from rotating relative to the first insert about the first axis and the third axis, the second insert having a third set of discrete opposing flats defined in its inner surface on opposing sides of the second insert, wherein flats of the third set of opposing flats are not connected to one another.

Still further, the method may include the step of securing a femoral head configured to be secured to a femoral stem to the second insert such that the outer surface of the femoral head contacts the inner surface of the second insert, the femoral head having a fourth set of discrete opposing flats defined in its outer surface on opposing sides of the femoral head, wherein flats of the fourth set of opposing flats are not connected to one another and wherein the fourth set of opposing flats contact the third set of opposing flats defined in the inner surface of the second insert; such that the femoral head is (i) permitted to rotate relative to the second insert about the third axis, and (ii) prevented from rotating relative to the second insert about the first axis and the second axis.

The step of securing the acetabular shell component to the acetabulum of a patient may occur before the steps of securing the first insert to the acetabular shell component, securing the second inset to the first insert, and securing the femoral head to the second insert.

The steps of securing the first insert to the acetabular shell component and securing the second insert to the first insert may occur before the step of securing the acetabular shell component to the acetabulum of the patient.

The method may further include the step of reaming the acetabulum of the patient to form a hemispherically shaped cavity prior to securing the acetabular shell component to the acetabulum of the patient.

The step of securing the acetabular shell component to the acetabulum of the patient may include press fitting, bolting, or cementing the acetabular shell component to the acetabulum.

The step of allowing the first insert to rotate relative to the acetabular shell component about a first axis may include the step of inserting a cylindrical wall extending outwardly from the first insert into an aperture formed in the acetabular shell component.

The step of allowing the first insert to rotate relative to the acetabular shell component about a first axis may include the step of aligning a projection extending outwardly from the acetabular shell component with a recess formed in the first insert.

The step of allowing the first insert to rotate relative to the acetabular shell component about a first axis may include the step of aligning a projection extending outwardly from the first insert with a recess formed in the acetabular shell component.

The method may include the steps of orienting the first axis to be orthogonal to the second axis and the third axis and orienting the second axis to be orthogonal to the third axis.

In another illustrative embodiment, a method for performing an orthopaedic surgical procedure on an acetabulum of a patient includes the steps of securing an acetabular shell component to an acetabulum of a patient and securing a first insert to an acetabular shell component configured to be implanted within an acetabulum of a patient, such that the first insert is (i) permitted to rotate relative to the acetabular shell component about a first axis, and (ii) prevented from rotating relative to the acetabular shell component about a second axis and a third axis, wherein the first insert having a first set of discrete opposing flats defined in its inner surface on opposing sides of the first insert, wherein flats of the first set of opposing flats are not connected to one another.

The method further includes the steps of securing a second insert to the first insert such that the outer surface of the second insert contacts the inner surface of the first insert, the second insert having a second set of discrete opposing flats defined in its outer surface on opposing sides of the second insert, wherein flats of the second set of opposing flats are not connected to one another and wherein the second set of opposing flats contact the first set of opposing flats defined in the inner surface of the first insert such that the second insert is (i) permitted to rotated relative to the first insert about the second axis, and (ii) prevented from rotating relative to the first insert about the first axis and the third axis and securing a femoral head configured to be secured to a femoral stem to the second insert such that the outer surface of the femoral head contacts the inner surface of the second insert.

Other aspects and advantages of the present disclosure will become apparent upon consideration of the following drawings and detailed description, wherein similar structures have similar reference numbers.

BRIEF DESCRIPTION OF THE DRAWINGS

The detailed description particularly refers to the following figures, in which.

DETAILED DESCRIPTION OF THE DRAWINGS

Figure 1:
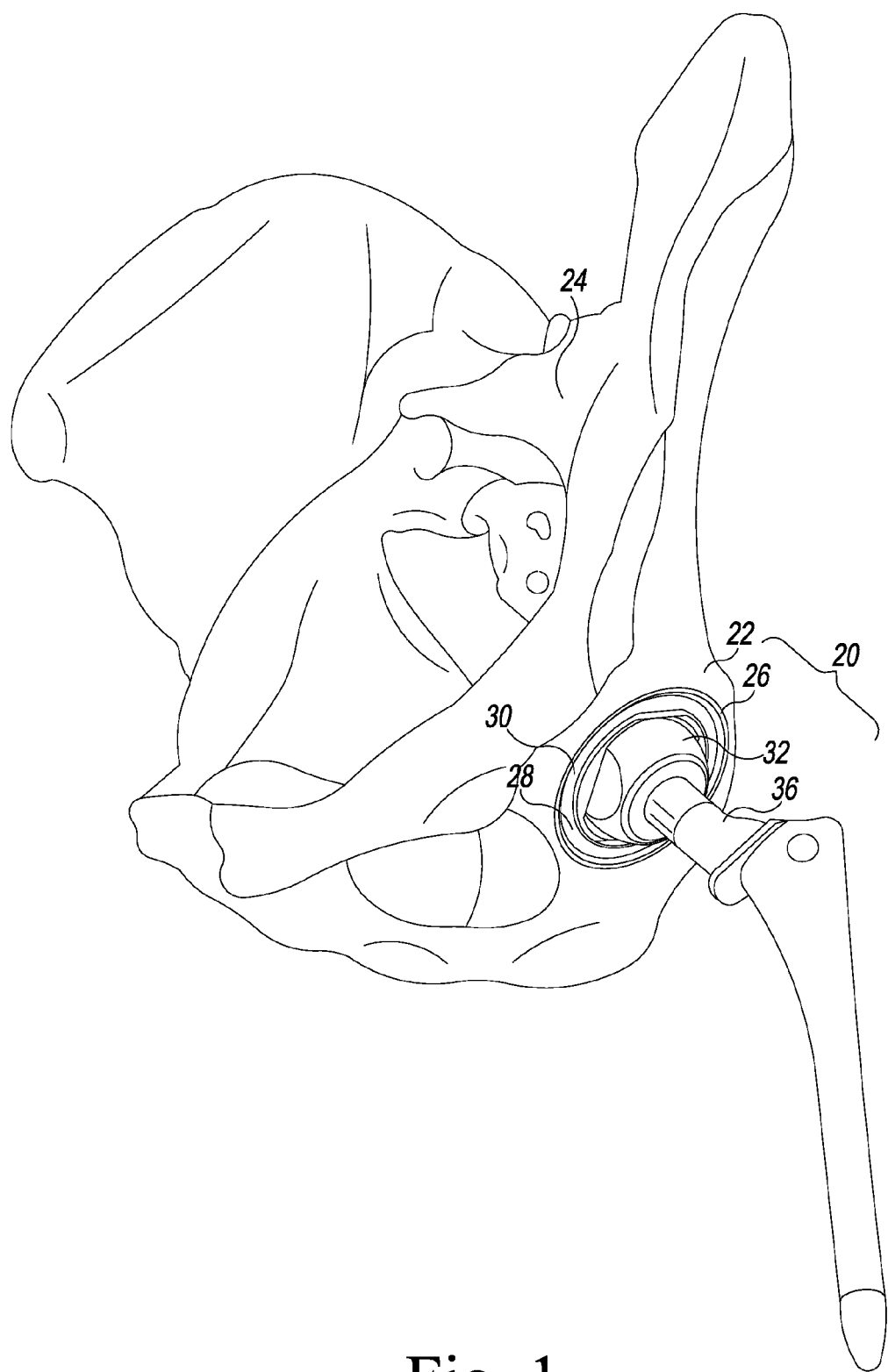
FIG. 1 is a perspective view of a first embodiment of an acetabular hip implant depicted within an acetabulum of a pelvic bone and further including a stem component extending from a femoral component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-3B, a first embodiment of an acetabular hip implant 20 is depicted within an acetabulum 22 of a human pelvic bone 24. The acetabular hip implant 20 generally includes an acetabular shell component 26, a metal insert 28, a polymer insert 30, and a femoral head component 32. The acetabular shell component 26 is generally configured to be implanted within the acetabulum 22 of a patient, as seen in FIG. 1. The metal insert 28 is configured to be received within and secured to the acetabular shell component 26, the polymer insert 30 is configured to be received within and secured to the metal insert 28, and the femoral head component 32 is configured to be received within and secured to the polymer insert 30, as will be described in greater detail hereinafter. The femoral head component 32 is configured to be secured to a femoral stem 36, which is configured to be implanted in femoral bone tissue (not shown) of the patient.

As seen in FIGS. 1-3B, the acetabular shell component 26 includes an outer surface 50 having a generally rounded shape that is hemispherical or at least partially spherical. The outer surface 50 is configured to be implanted within the acetabulum 22 using any method or structure known in the art. The acetabular shell component 26 further includes an inner surface 52 that is partially spherical in shape. In one version, as seen in FIGS. 2A and 2B, a protrusion 70 is formed within or otherwise attached to the inner surface 52 of the acetabular shell component 26. The protrusion 70 in this embodiment is an outwardly extending projection that cooperates with a feature within the metal insert 28 to allow rotation of the metal insert 28 with respect to the acetabular shell component 26 about an axial axis 72, as will be discussed in greater detail below.

Figure 2A:
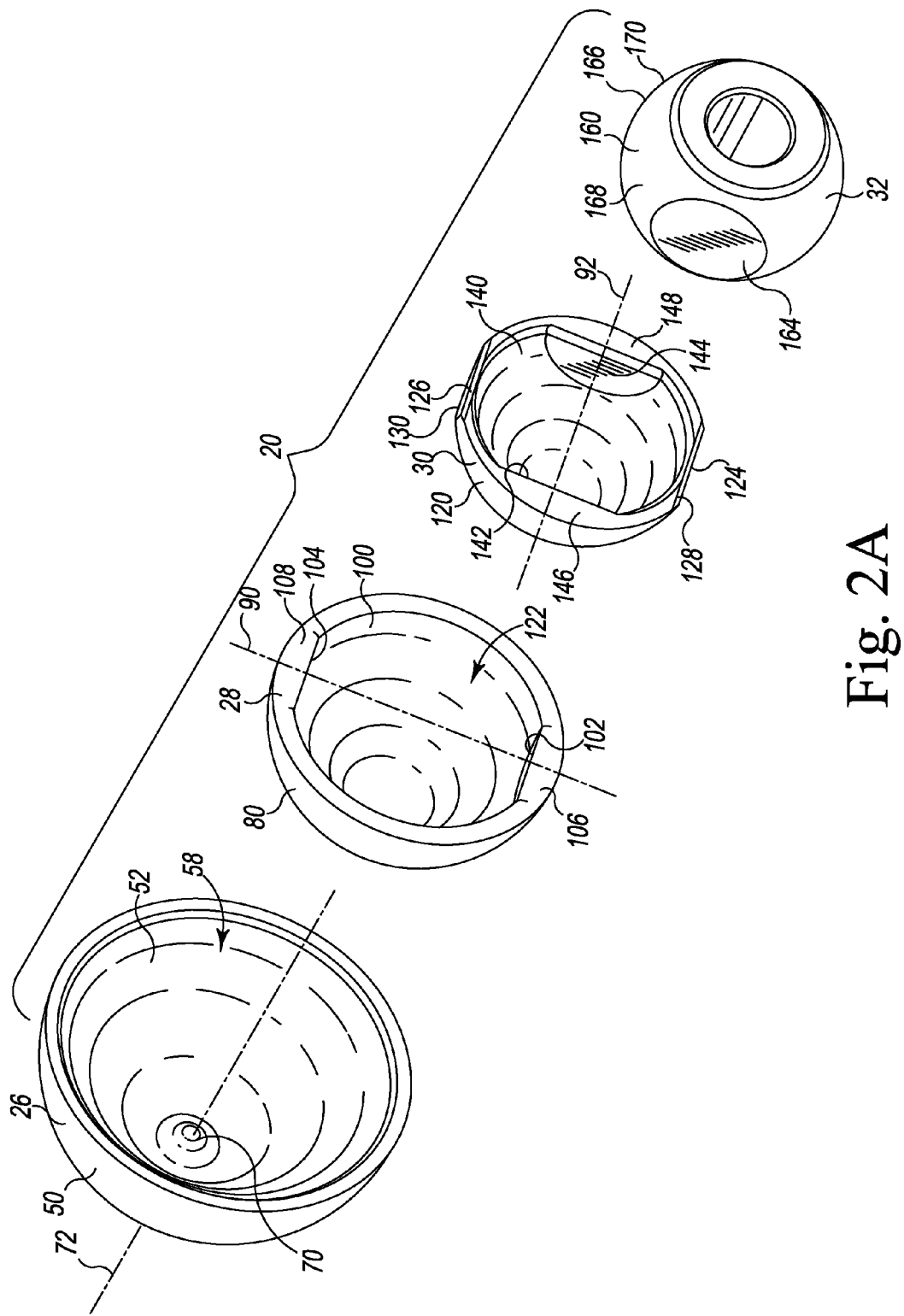
FIG. 2A is an exploded perspective view of a first version of the acetabular hip implant of FIG. 1.
Figure 2B:
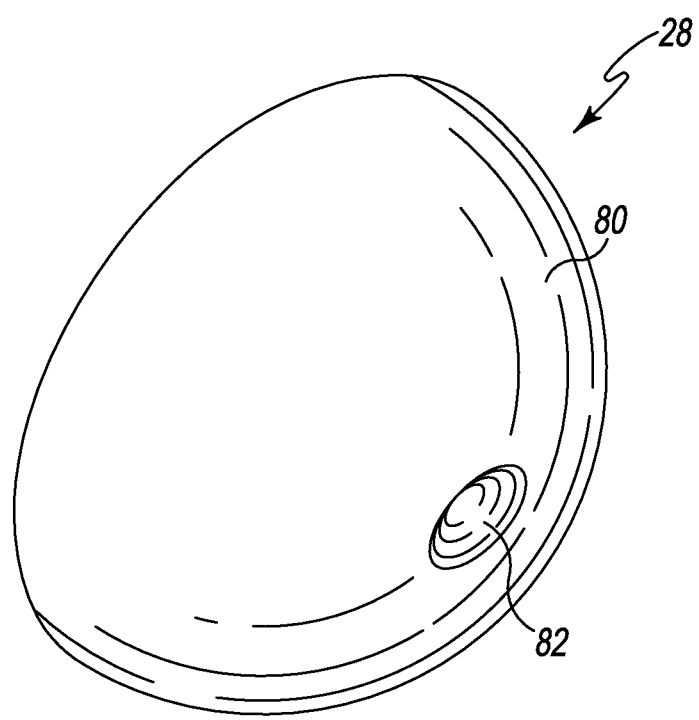
FIG. 2B is a rear perspective view of a metal insert of the acetabular hip implant of the first embodiment of the acetabular hip implant of FIG. 1.
Figure 3A:
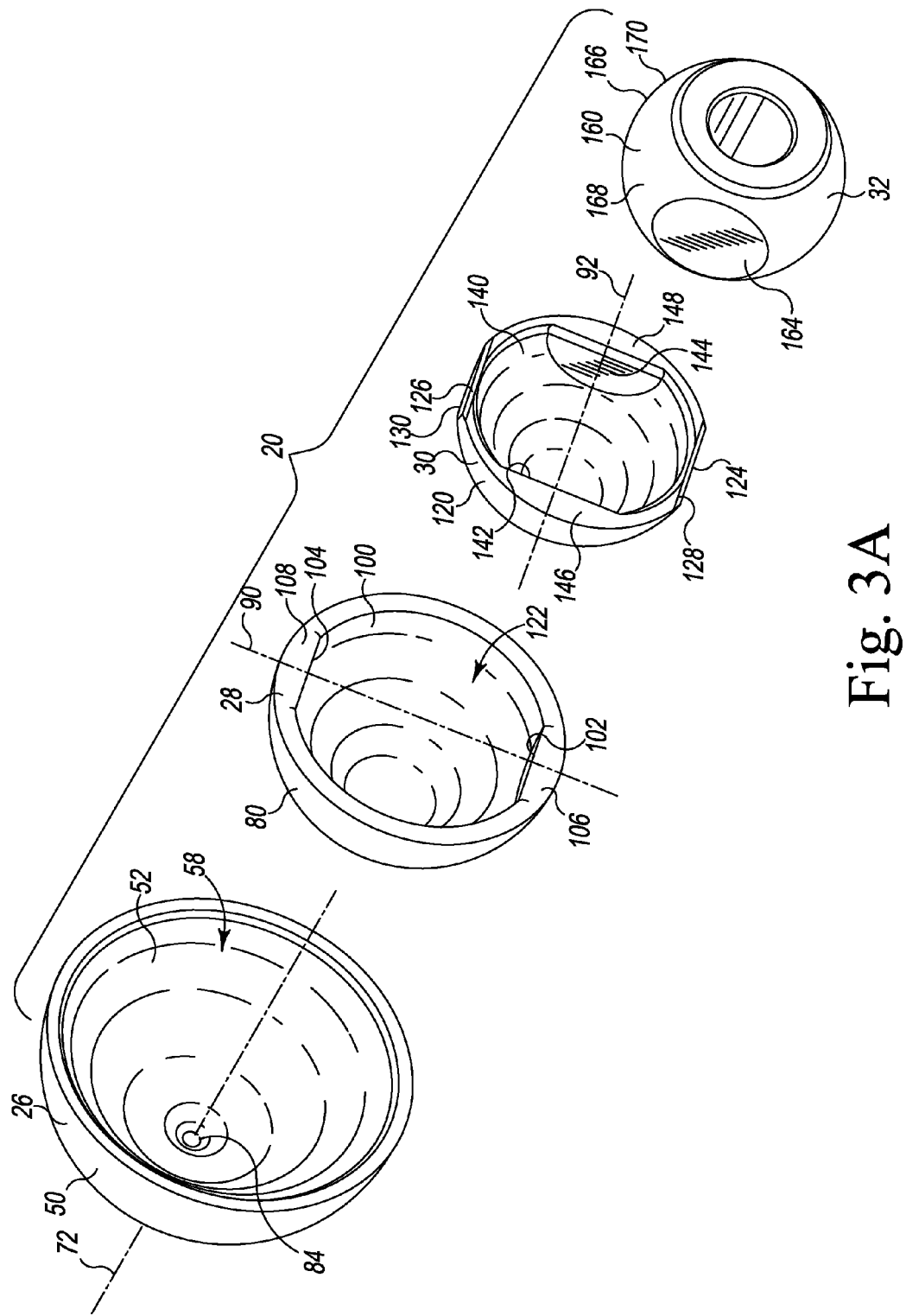
FIG. 3A is an exploded perspective view of a second version of the acetabular hip implant of FIG. 1.
Figure 3B:
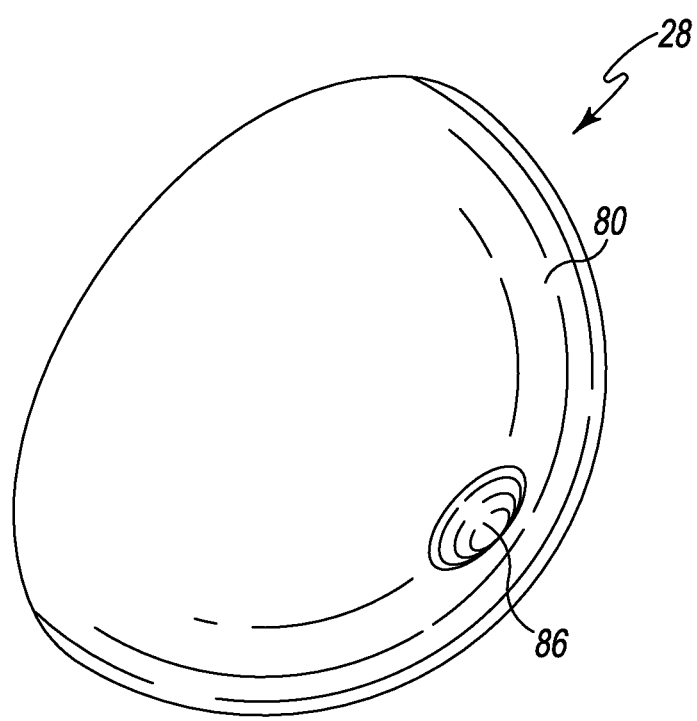
FIG. 3B is a rear perspective view of a metal insert of the acetabular hip implant of the second embodiment of the acetabular hip implant of FIG. 1.

The metal insert 28, as best seen in FIG. 2A, includes an outer surface 80 having a generally hemispherical or at least partially spherical shape and having a size that is slightly smaller than a size of the inner surface 52 of the acetabular shell component 26. As noted above, the outer surface 80 of the metal insert 28 is configured to be received and secured within a cavity 58 formed by the inner surface 52 of the acetabular shell component 26. A recess 82 is formed within the outer surface 80 of the metal insert 28 (as seen in FIG. 2B), wherein the recess 82 cooperates with the protrusion 70 in the inner surface 52 of the acetabular shell component 26 to allow the metal insert 28 to rotate relative to the acetabular shell component 26 about the axial axis 72. While the acetabular shell component 26 is shown having an outwardly extending element (protrusion 70) and the metal insert 28 is shown having an inwardly extending element (recess 82), such elements may be reversed and/or other elements that cooperate to allow rotation of the metal insert 28 relative to the acetabular shell component 26 about the axial axis 72 may be utilized. For example, as seen in FIGS. 3A and 3B, the acetabular shell component 26 of FIG. 3A includes a recess 84 and the metal insert 28 of FIG. 3B includes a protrusion 86 that cooperates with the recess 84 to allow rotation of the metal insert relative to the acetabular shell component 26 about the axial axis 72.

In addition to allowing rotation about the axial axis 72, the protrusion 70 and recess 82 (or the recess 84 and protrusion 86) cooperate to prevent rotation of the metal insert 28 with respect to the acetabular shell component 26 about any other axes, including an abduction axis 90 and a flexion axis 92. The axial axis 72, in the embodiments shown herein, is orthogonal to the abduction axis 90 and the flexion axis 92, and the abduction axis 90 is orthogonal to the flexion axis 92.

Referring again to FIG. 2, the metal insert 28 further includes an inner surface 100 that is generally partially spherical in shape. A set of opposing flats 102, 104 is defined in the inner surface 100 on opposing sides 106, 108, respectively, of the metal insert 28. The flats 102, 104 in this embodiment, are generally perpendicular to the abduction axis 90. The flats 102, 104 are also parallel to each other. The function of the flats 102, 104 will be described in greater detail below.

The polymer insert 30, as best seen in FIG. 2, includes an outer surface 120 having a generally hemispherical or at least partially spherical shape and having a size that is slightly smaller than a size of a cavity 122 formed by the inner surface 100 of the metal insert 28. The outer surface 120 of the polymer insert 30 is configured to be received and secured within the cavity 122. The outer surface 120 of the polymer insert 30 further includes a set of opposing flats 124, 126 defined in opposing sides 128, 130, respectively, of the outer surface 120 of the polymer insert 30. The flats 124, 126 are generally perpendicular to the abduction axis 90. The flats 124, 126 are also generally parallel to each other and generally parallel to the metal insert's flats 102, 104.

Referring to FIG. 1, when the polymer insert 30 is inserted into the metal insert 28, the flats 124, 126 of the polymer insert 30 are in contact with the flats 102, 104 of the metal insert 28, respectively. In fact, due to the sizes and shapes of the metal and polymer inserts 28, 30, the polymer insert 30 will only fit within the metal insert 28 with the polymer insert's flats 124, 126 in contact with the metal insert's flats 102, 104 in such a manner. The flats 102, 104 create a bearing surface that allow the polymer insert 30 to rotate relative to the metal insert 28 about the abduction axis 90. This arrangement also prevents rotation of the polymer insert 30 relative to the metal insert 28 about any other axis, including about the axial axis 72 and the flexion axis 92.

The polymer insert 30 further includes an inner surface 140 that is generally partially spherical in shape. A set of opposing flats 142, 144 is defined within the inner surface 140 on opposing sides 146, 148, respectively, of the polymer insert 30. The opposing flats 142, 144, in this embodiment, are generally perpendicular to the flexion axis 92. The opposing flats 142, 144 are also parallel to each other. The function of the opposing flats 142, 144 will be described in greater detail hereinafter.

Still referring to FIG. 2, the femoral head component 32 includes an outer surface 160 having a generally spherical shape and having a size that is slightly smaller than the size of a cavity formed by the inner surface 140 of the polymer insert 30. The femoral head component 32 is configured to be received by and secured within the cavity formed by the inner surface 140 of the polymer insert 30. The outer surface 160 of the femoral head component 32 further includes a set of opposing flats 164, 166 on opposing sides 168, 170 of the femoral head component 32. The opposing flats 164, 166 are generally perpendicular to the flexion axis 92. The opposing flats 164, 166 are also generally parallel to each other and generally parallel to the opposing flats 142, 144 of the polymer insert 30. The flats 142, 144 of the polymer insert 30 and the flats 164, 166 of the femoral head component 32 are also orthogonal to the flats 102, 104 of the metal insert 28 and the flats 124, 126 of the polymer insert 30.

Referring to FIG. 1, when the femoral head component 32 is inserted into the polymer insert 30, the opposing flats 164, 166 of the femoral head component 32 are positioned in contact with the opposing flats 142, 144 of the polymer insert 30, respectively. In fact, due to the sizes and shapes of the polymer insert 30 and the femoral head component 32, the femoral head component 32 will only fit within the polymer insert 30 with the opposing flats 164, 166 of the femoral head component 32 positioned in contact with the opposing flats 142, 144 of the polymer insert 30, respectively. The opposing flats 142, 144 creates a bearing surface that allows the femoral head component 32 to rotate with respect to the polymer insert 30 about the flexion axis 92. This arrangement also prevents rotation of the femoral head component 32 with respect to the polymer insert 30 about any other axis, including about the axial axis 72 and the abduction axis 90.

Figure 4:
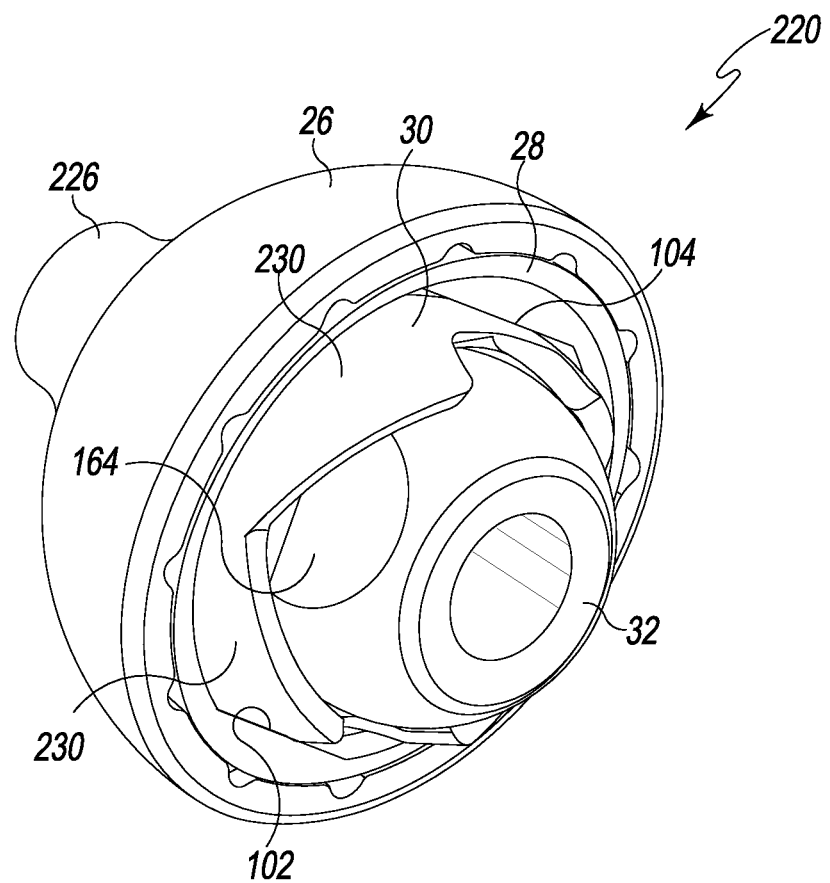
FIG. 4 is a perspective view of a second embodiment of an acetabular hip implant.
Figure 5:
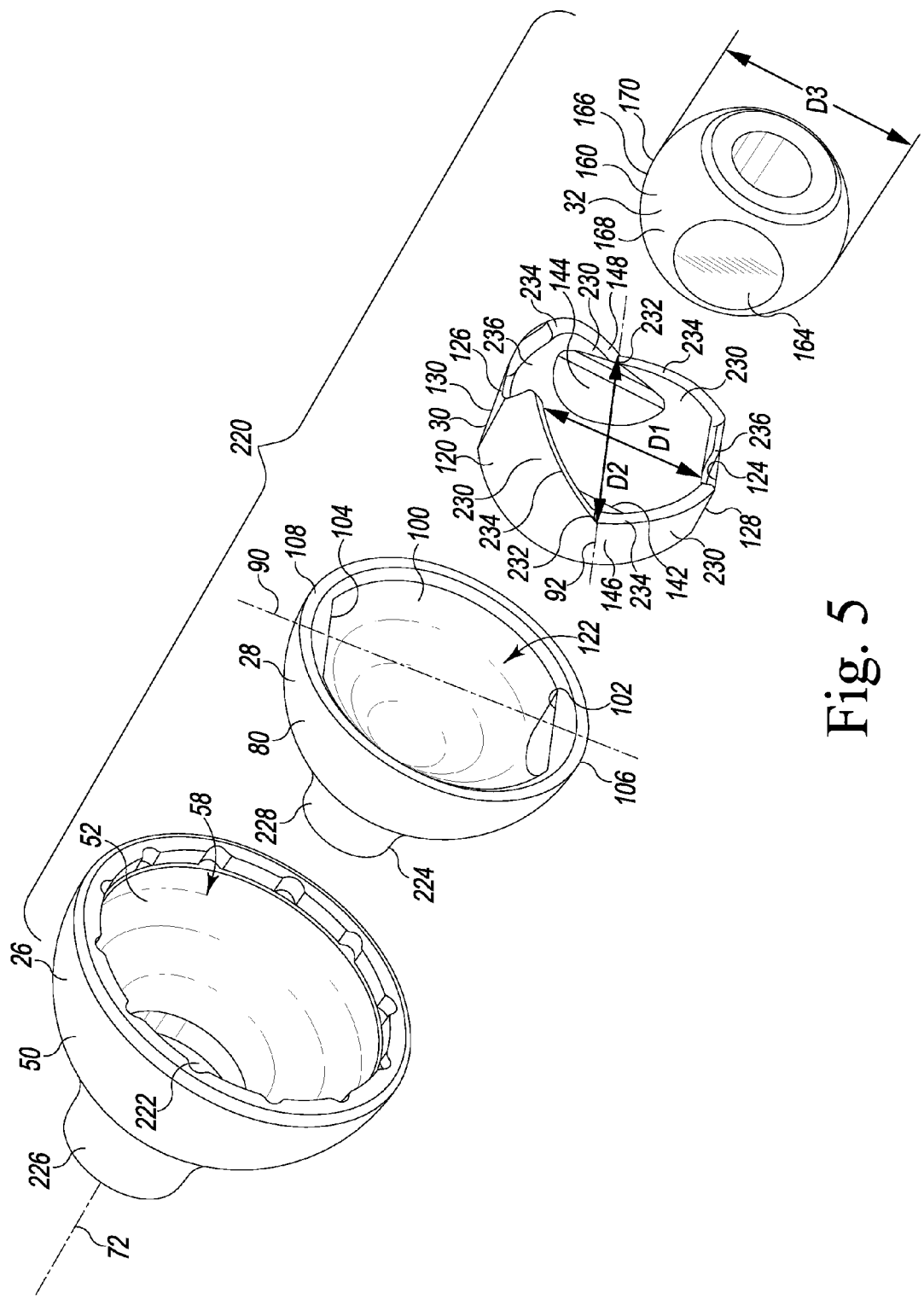
FIG. 5 is an exploded perspective view of the acetabular hip implant of FIG. 4.

It will be appreciated that the principles of the present disclosure and at least some of the benefits may be carried out in a number of different ways. For example, FIGS. 4 and 5 depict an alternative embodiment of an acetabular hip implant 220. The acetabular hip implant 220 is similar to the acetabular hip implant of FIGS. 1 and 2 and, thus, only the differences will be described. In the acetabular hip implant 220, the protrusion 70 has been replaced by an aperture 222 and the recess 82 has been replaced by a projection 224. In particular, the aperture 222 is formed by an outwardly extending generally cylindrical wall 226 and the projection 224 is formed by an outwardly extending generally cylindrical wall 228 having a diameter slightly less than the diameter of the aperture 222. When the acetabular hip implant 220 is assembled, the projection 224 fits and is retained within the aperture 222. As with the embodiment of FIGS. 1 and 2, such an arrangement allows rotation of the metal insert 28 relative to the acetabular shell component 26 about the axial axis 72, but prevents rotation about any other axes, including the abduction axis 90 and the flexion axis 92. As would be understood by one skilled in the art and as discussed above, the cylindrical walls 226, 228 may take other forms.

Still referring to FIGS. 4 and 5, the acetabular hip implant 220 includes an additional constraint that aids in retaining the femoral head component 32 within the polymer insert 30. In particular, the polymer insert 30 includes a plurality of extensions 230 that are integral with and extend outwardly from the polymer insert 30. The extension 230 are generally spherical in shape and extend outwardly beyond outermost ends of the acetabular shell component 26 and the metal insert 28. As seen in FIGS. 4 and 5, the extensions 230 form opposing V-shaped openings 232, which are formed by generally straight edges 234, and opposing C-shaped openings 236. The distance D1 between opposing extensions 230 is less than an inner diameter D2 of the polymer insert 30 and a diameter D3 of the femoral head component 32. Therefore, the extensions 230 aid in retaining the femoral head component 32 within the polymer insert 30. The V-shaped openings 232 and the C-shaped openings 236 provide some resilience and flexibility to the extensions 230 to allow the femoral head component 34 to be inserted into the polymer insert 30 when enough force is exerted, while providing resistance to dislocation of the femoral head component 34 from the polymer insert 30.

Figure 6:
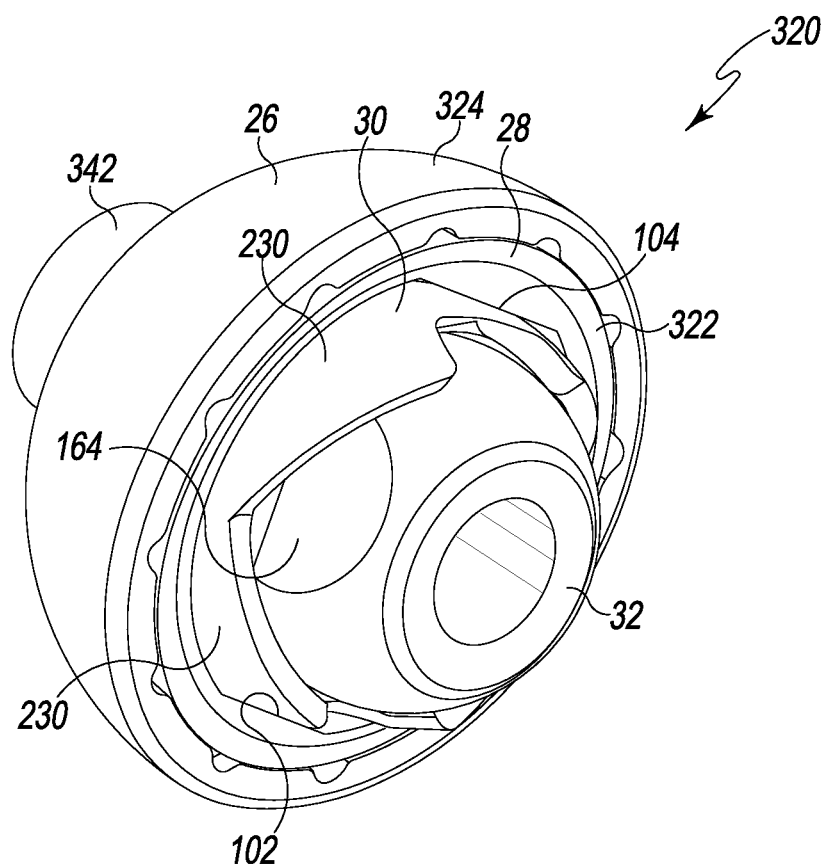
FIG. 6 is a perspective view of a third embodiment of an acetabular hip implant.
Figure 7:
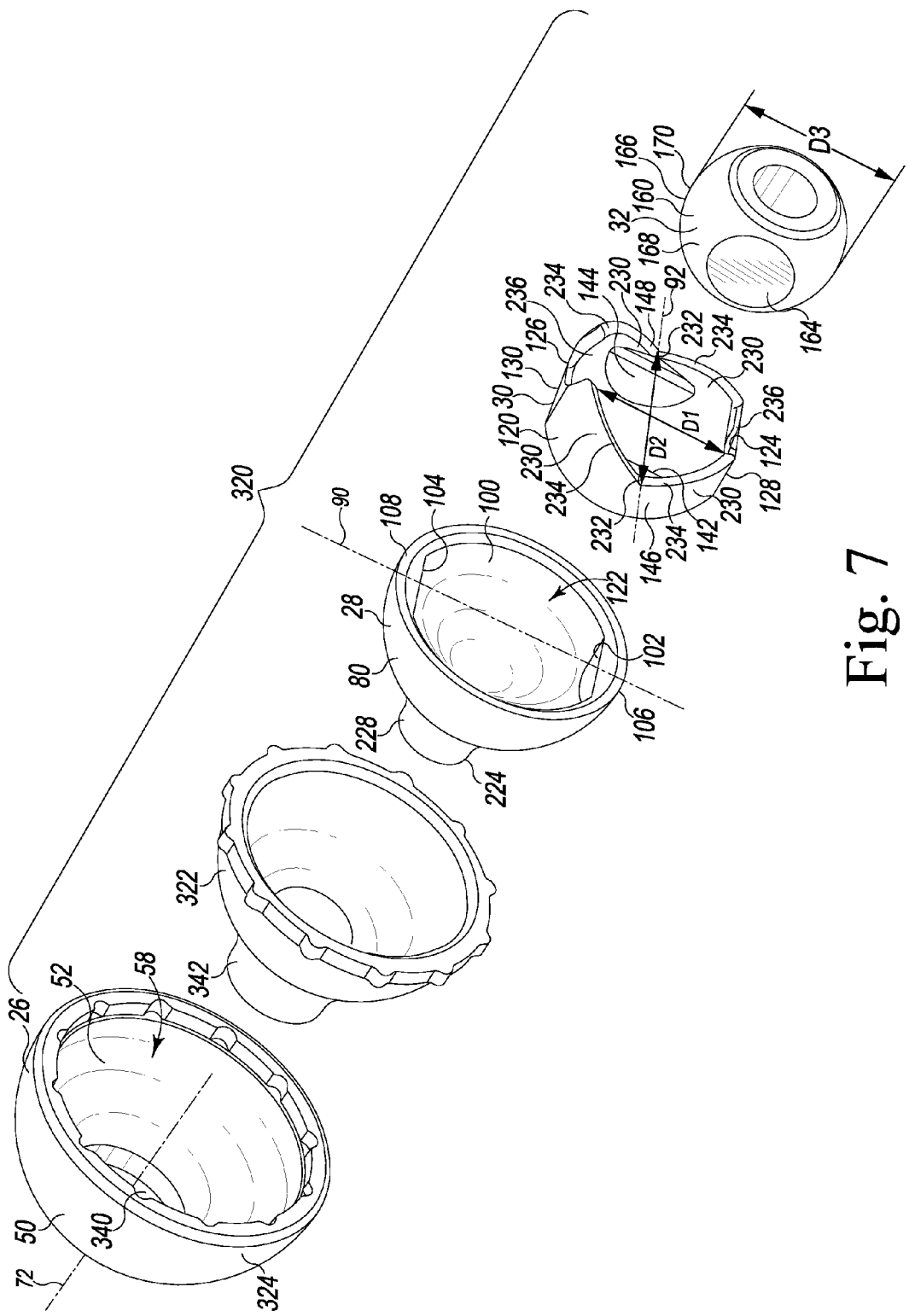
FIG. 7 is an exploded perspective view of the acetabular hip implant of FIG. 6.

Referring now to FIGS. 6 and 7, yet another embodiment of an acetabular hip implant 320 that is similar to the acetabular hip implant of FIGS. 4 and 5 is shown. In this embodiment, the acetabular shell component 26 is modular. In particular, the acetabular shell component 26 includes a polymer component 322 and a metal component 324, wherein the polymer component 322 is retained within and secured to the metal component 324.

The acetabular shell component 26 of FIGS. 6 and 7 also includes an aperture 340 formed through the acetabular shell component 26. The cylindrical wall 228 and a cylindrical wall 342 extending from the polymer component 322 extend through the aperture 340 and an inner surface of the cylindrical wall 342 forms a hearing surface against which the cylindrical wall 228 bears to allow the metal insert 28 to rotate with respect to the axial axis 72.

Figure 8:
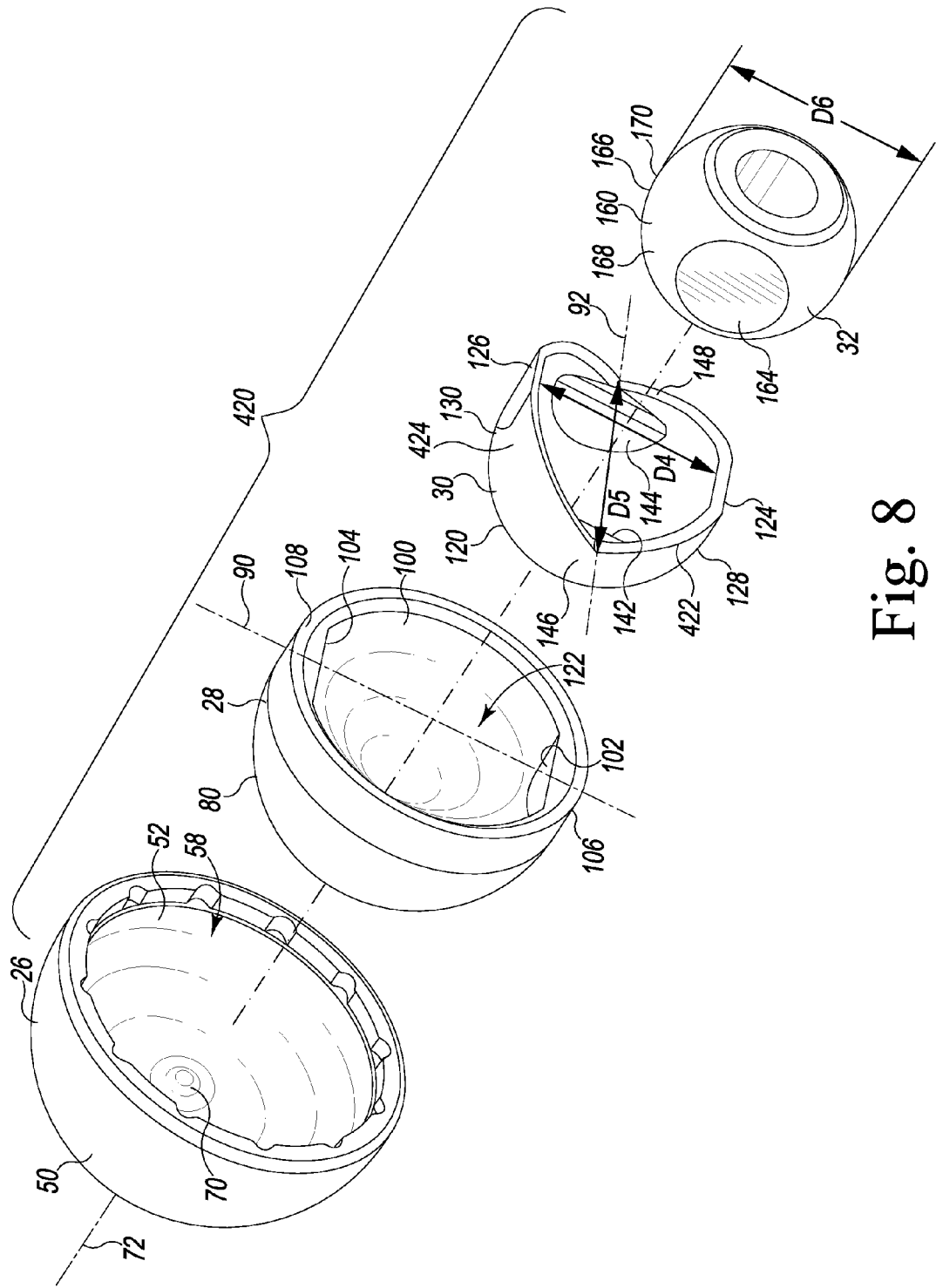
FIG. 8 is an exploded perspective view of a fourth embodiment of an acetabular hip implant.

Referring now to FIG. 8, a further embodiment of an acetabular hip implant 420 that is similar to the embodiment of FIGS. 1 and 2 is shown. In this embodiment, the polymer insert 30 includes opposing extensions 422, 424 that are spherical in shape and follow the curvature of the polymer insert 30. Similar to the extensions 230 of the embodiment of FIGS. 6 and 7, a distance D4 between the extensions 422, 424 is less than an inner diameter D5 of the polymer insert 30 and a diameter D6 of the femoral head component 32. The extensions 422, 424 are resilient enough to allow the femoral head to be inserted into the polymer insert 30 when enough force is exerted, yet provide resistance to dislocation of the femoral head component 32 from the polymer insert 30.

The acetabular shell component 26 of any of the acetabular hip implants disclosed herein may be formed of any combination of metal, ultra-high molecular weight polyethylene (UHMWPE), ceramic, polyetheretherketone (PEEK), or any other materials known in the art. In one exemplary embodiment, the acetabular shell component 26 includes a metal shell having an inner surface lined with a polymeric material (or a separate polymeric component attached to the metal shell, as in FIGS. 6 and 7). The polymeric material may be an ultra-high molecular weight polyethylene (UHMWPE) and the metal may be a higher hardness alloy, such as an alloy of cobalt and chromium, for example CoCrMo. The polymeric liner may be locked, molded, or otherwise secured to the metal shell. In another example, the acetabular shell component 26 has a metal shell with an external surface that is provided with a coating that promotes ingrowth of hone tissue. For example, the external surface of the metal shell may have a porous structure, for example, a coating of cobalt-chromium alloy beads, such as a product sold by DePuy Orthopaedics Inc. under the trade mark POROCOAT®. Optionally, the external surface of the metal shell may be provided with a coating of an additional or alternative material that promotes bone ingrowth, such as a hydroxyapatite material.

The metal and polymer inserts 28, 30 and the femoral head component 32 may be formed of a ceramic, polymeric, metallic, PEEK, or any other material known in the art or as described herein, or combinations thereof.

The components 26, 28, 30, 32 of the acetabular hip implant 20 may have alternating materials, such that no two adjacent components are made of the same material. In particular, the alternating materials alternate between hard and polymeric materials. Examples of hard materials are metal, ceramic, or PEEK and an example of a polymeric material is UHMWPE. Different types of hard and polymeric materials may be utilized (e.g., for example, different metals may be used for the hard components or a metal may be used for one hard component and ceramic for another). In one exemplary embodiment, the acetabular shell component 26 includes a metal shell having an inner surface lined with a polymeric material, the metal insert is made of a metallic material, the polymer insert is made of a polymeric material, and the femoral component is made of a metallic material. In a further exemplary embodiment, the acetabular shell component 26 includes is a metal monoblock, the insert adjacent the shell component 26 is made of a polymeric material, the other insert is made of a metallic material, and the femoral component is made of a polymeric material.

Although the axes 72, 90, 92 are described as aligning with the anatomical axes (i.e., axial, abduction, and flexion), the axes 72, 90, 92 may alternatively be aligned in another manner, so long as the axes 72, 90, 92 are orthogonal to one another.

The acetabular hip implants disclosed herein allow the three basic motions of the hip to be broken down into three different movements. The combined rotational capabilities of these three different movements, namely, movement of the metal insert 28 with respect to the shell 26 about the axial axis 72, movement of the polymer insert 30 with respect to the metal insert 28 about the abduction axis 90, and movement of the femoral head component 32 with respect to the polymer insert 30 about the flexion axis 92, provide a large range of motion of the femoral head component 32 relative to the acetabular shell component 26. While two liners 28, 30 are depicted in the figures herein, it should be understood that a single liner 28 or 30 may be utilized.

While a projection and aperture or other similar features are shown as allowing rotation about the axial axis and sets of flats are shown as allowing rotation about the abduction and flexion axes, the projection and aperture could alternatively be utilized for rotation about the abduction axis or the flexion axis and the sets of flats may be utilized for rotation about the axial axis. For example, the projection and the aperture of the shell 26 and the liner 28 would be switched with the flats of the liners 28, 30 or with the flats of the liner 30 and the femoral head component 32.

In addition, while each of the opposing sets of flats are depicted as having two parallel flats, each set of flats may alternatively be replaced by a single flat.

In an exemplary implementation, the acetabular implant 20 is used in a total hip replacement procedure. A surgical method for implanting the acetabular hip implant 20 of FIGS. 1 and 2 involves assembling the components 26, 28, 30, and 32 of the acetabular hip implant 20 and implanting the acetabular hip implant 20 within the acetabulum 22 of the patient while supporting the femoral stem 36 within the femoral bone tissue.

In further detail, a reamer, not shown, is typically used to ream or otherwise cut the acetabulum 22 in order to form a hemispherically shaped cavity. The surgeon may then implant either final components or trial fit components. Trial fitting is well known in the art and assists the surgeon in final preparation of the acetabulum and in choosing the proper sizes of the various components of the acetabular hip implant 20.

After suitable trial fitting, the trial implant is removed and the surgeon may then implant the acetabular shell component 26 into the acetabulum 22. The acetabular shell component 26 may be press fit, bolted, cemented or otherwise attached to the acetabulum 22, as is well known in the art.

In a first exemplary procedure, the acetabular shell component 26 is implanted into the acetabulum 22 separately and then the metal insert 28 is pressed into the acetabular shell component 26 in vivo. The metal insert 28 is aligned with the acetabular shell component 26 such that the protrusion 70 of the acetabular shell component 26 is received within the recess 82 of the metal insert 28 to allow rotation of the metal insert 28 with respect to the acetabular shell component 26 about the axial axis 72. The acetabular shell component 26 is therefore stationary and the metal insert 28 rotates about the axial axis 72.

The polymer insert 30 is pressed into the metal insert 28 in vivo. Optionally, the polymer insert 30 may be pressed into the metal insert 28 external to the acetabulum 22. As noted above, the polymer insert 30 is aligned with the metal insert 28 such that the opposing flats 124, 126 of the polymer insert 30 are in contact with the opposing flats 102, 104 of the metal insert 28. The positioning and shape of the opposing flats 102, 104 and the opposing flats 124, 126 allow the polymer insert 30 to rotate with respect to the metal insert 28 about the abduction axis 90. The metal insert 28 is therefore stationary with respect to the abduction axis 90.

Once the metal and polymer inserts 28, 30 are secured, the surgeon secures the femoral head component 32 within the polymer insert 30. The femoral stem 36 may already be implanted within the femoral bone tissue or may be implanted within the femoral bone tissue after the femoral head component 32 is secured within the polymer insert 30. To secure the femoral head component 32 within the polymer insert 30, the femoral head component 32 is pressed into the polymer insert 30 with the opposing flats 164, 166 of the femoral head component 32 positioned in contact with the opposing flats 142, 144 of the polymer insert 30, respectively. The positioning and shape of the opposing flats 142, 144 and the opposing flats 164, 166 allow the femoral head component 32 to rotate with respect to the polymer insert 30 about the flexion axis 92. The polymer insert 30 is therefore stationary with respect to the flexion axis 92.

In the embodiment described above, the components of the acetabular hip implant 20 are assembled in vivo. Alternatively, any of the components (or all) may instead be assembled external to the acetabulum 22 prior to implantation. In addition or alternatively, one skilled in the art should understand that the same steps may be utilized (minus insertion of the polymer insert 30 into the metal insert 28) if the polymer insert 30 is omitted.

As will become apparent from reading the present specification, any of the features of any of the embodiments disclosed herein may be incorporated within any of the other embodiments without departing from the scope of the present disclosure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An acetabular hip implant, comprising:
an acetabular shell component configured to be implanted within an acetabulum of a patient, the acetabular shell component having an inner surface that is partially spherical and having an axis, a first insert secured to the acetabular shell component and having an outer surface that is partially spherical such that the first insert is (i) permitted to rotate relative to the acetabular shell component about a first axis defined by the axis of shell component, and (ii) prevented from rotating relative to the acetabular shell component about second and third axes each of which is perpendicular to the first axis and to the other of the second and third axes, the first insert having a first pair of opposing flats which are parallel to one another and perpendicular to the second axis, a second insert secured to the first insert such that an outer surface of the second insert contacts an inner surface of the first insert, the second insert having a second pair of opposing flats defined in its outer surface which are parallel to one another and perpendicular to the second axis, each of the flats of the second pair contacting a respective flat of the first pair such that the second insert is (i) permitted to rotate relative to the first insert about the second axis, and (ii) prevented from rotating relative to the first insert about the first and third axes, the second insert having an inner surface with a third pair of opposing flats defined therein which are parallel to one another and perpendicular to the third axis, and a femoral head configured to be secured to a femoral stem, the femoral head being secured to the second insert such that an outer surface of the femoral head contacts the inner surface of the second insert, the femoral head having a fourth pair of opposing flats defined in its outer surface, each of the flats of the fourth pair contacting a respective flat of the third pair such that the femoral head is (i) permitted to rotate relative to the second insert about the third axis, and (ii) prevented from rotating relative to the second insert about the first and second axes, wherein the flats defined in the inner surface of the first insert are provided on opposing sides of the first insert, the flats defined in the outer surface of the second insert are provided on opposing sides of the second insert, the flats defined in the inner surface of the second insert are provided on opposing sides of the second insert, and the flats defined in the outer surface of the femoral head are provided on opposing sides of the femoral head, and wherein an entire portion of each flat of each pair of opposing flats includes a planar surface.

2. The hip implant of claim 1, in which the acetabular shell component comprises a polymeric liner locked to a metal shell.

3. The hip implant of claim 1, in which the acetabular shell component comprises a polymeric liner moulded to a metal shell.

4. The hip implant of claim 1, in which the acetabular shell component includes a metal shell having an inner surface lined with a polymeric material, the first insert and the femoral head are made of metal, and the second insert is made of a polymeric material.

5. The hip implant of claim 1, in which the acetabular shell component comprises a protrusion received into a recess in the first insert to allow rotation about the first axis and prevent rotation about the second axis or the third axis.

6. An acetabular hip implant, comprising:

an acetabular shell component configured to be implanted within an acetabulum of a patient, a first insert secured to the acetabular shell component such that the first insert is (i) permitted to rotate relative to the acetabular shell component about a first axis, and (ii) prevented from rotating relative to the acetabular shell component about a second axis and a third axis, the first insert having a first set of opposing flats defined in its inner surface, a second insert secured to the first insert such that an outer surface of the second insert contacts the inner surface of the first insert, the second insert having a second set of opposing flats defined in its outer surface contact the first set of opposing flats defined in the inner surface of the first insert such that the second insert is (i) permitted to rotate relative to the first insert about the second axis, and (ii) prevented from rotating relative to the first insert about the first axis and the third axis, the second insert having a third set of opposing flats defined in its inner surface and further including a plurality of extensions integral with and extending outwardly from the second insert, wherein a distance between opposing extensions is less than an inner diameter of the second insert, and a femoral head configured to be secured to a femoral stem, the femoral head being secured to the second insert such that an outer surface of the femoral head contacts the inner surface of the second insert, the femoral head having a fourth set of opposing flats defined in its outer surface that contact the third set of opposing flats defined in the inner surface of the second insert such that the femoral head is (i) permitted to rotate relative to the second insert about the third axis, and (ii) prevented from rotating relative to the second insert about the first axis and the second axis, wherein an entire portion of each flat of each set of opposing flats includes a planar surface.

7. The acetabular hip implant of claim 6, wherein the distance between opposing extensions is less than a diameter of the femoral head.

8. The acetabular hip implant of claim 6, wherein the extensions are formed by alternating V-shaped openings and C-shaped openings.

9. The acetabular hip implant of claim 6, wherein the extensions are spherical in shape.

* * * * *